United States Patent
Ganley et al.

(10) Patent No.: US 7,092,780 B2
(45) Date of Patent: Aug. 15, 2006

(54) METHOD FOR PRODUCING DENTAL RESTORATION AND APPARATUS THEREFOR

(75) Inventors: Robert Ganley, Williamsville, NY (US); Thomas J. Hill, Amherst, NY (US); Eric Cunningham, Malden, MA (US); John DePiano, Burlington, MA (US)

(73) Assignee: Ivoclar Vivadent A.G., Schaam (LI)

( * ) Notice: Subject to any disclaimer, the term of this patent is extended or adjusted under 35 U.S.C. 154(b) by 0 days.

(21) Appl. No.: 10/866,425

(22) Filed: Jun. 10, 2004

(65) Prior Publication Data

US 2004/0254667 A1    Dec. 16, 2004

Related U.S. Application Data

(60) Provisional application No. 60/478,209, filed on Jun. 13, 2003.

(51) Int. Cl.
*G06F 19/00* (2006.01)
*A61C 5/08* (2006.01)

(52) U.S. Cl. .................. 700/117; 700/98; 433/223; 433/24

(58) Field of Classification Search .............. 700/97, 700/98, 182, 159, 163, 197, 117, 118; 425/56, 425/451.9; 433/24, 202.1, 215, 223; 264/16, 264/19
See application file for complete search history.

(56) References Cited

U.S. PATENT DOCUMENTS

| | | | |
|---|---|---|---|
| 3,861,044 A | | 1/1975 | Swinson |
| 4,324,546 A | | 4/1982 | Heitlinger |
| 4,515,634 A | * | 5/1985 | Wu et al. ................ 433/202.1 |
| 4,575,805 A | | 3/1986 | Moermann |
| 4,611,288 A | | 9/1986 | Duret |
| 4,663,720 A | | 5/1987 | Duret |
| 5,273,429 A | | 12/1993 | Rekow |
| 5,452,219 A | | 9/1995 | Dehoff |
| 5,691,905 A | | 11/1997 | Dehoff |
| 5,718,585 A | | 2/1998 | Dehoff |
| 6,488,503 B1 | * | 12/2002 | Lichkus et al. .............. 264/19 |
| 6,691,764 B1 | * | 2/2004 | Embert et al. ............. 433/223 |
| 6,808,659 B1 | * | 10/2004 | Schulman et al. ........... 264/16 |
| 6,984,261 B1 | * | 1/2006 | Cummings et al. ......... 433/215 |
| 2003/0096214 A1 | | 5/2003 | Luthardt |

* cited by examiner

Primary Examiner—Leo Picard
Assistant Examiner—Charles Kasenge
(74) Attorney, Agent, or Firm—John C. Thompson; Alan S. Korman

(57) ABSTRACT

A method for producing a dental restoration wherein a tooth preparation area is scanned either directly or indirectly. The scanned data is used by a computer controlled milling machine to create two or more investment blocks (50, 52, 54) for preparing a suitable dental restoration, the investment blocks being of a material which may be used in ovens operating in a 800° to 1,200° C. range. A suitable dental restorative material (18) and the blocks are place in an oven, and after being clamped together, the material (18) is pressed or injected into the investment blocks to form the desired dental restoration. Subsequently, after cooling, the dental restoration is divested from the investment mold and finished.

11 Claims, 7 Drawing Sheets

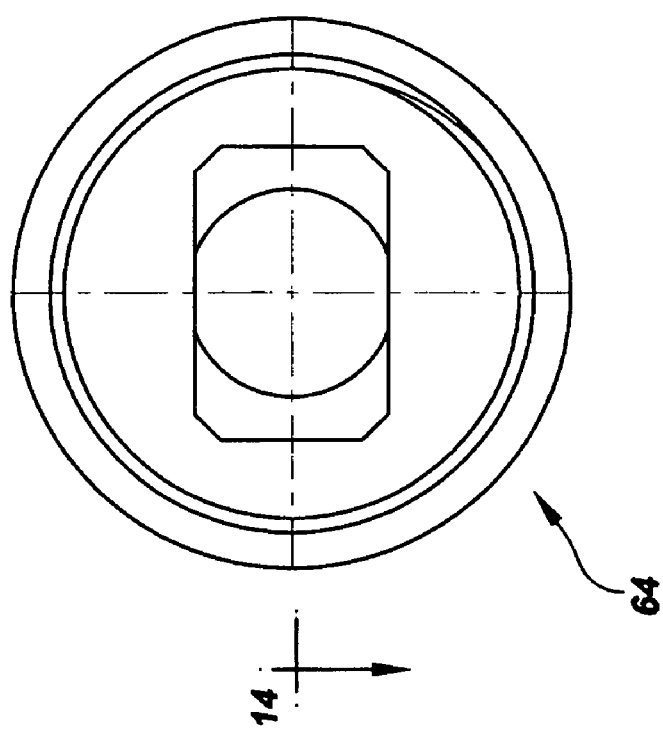
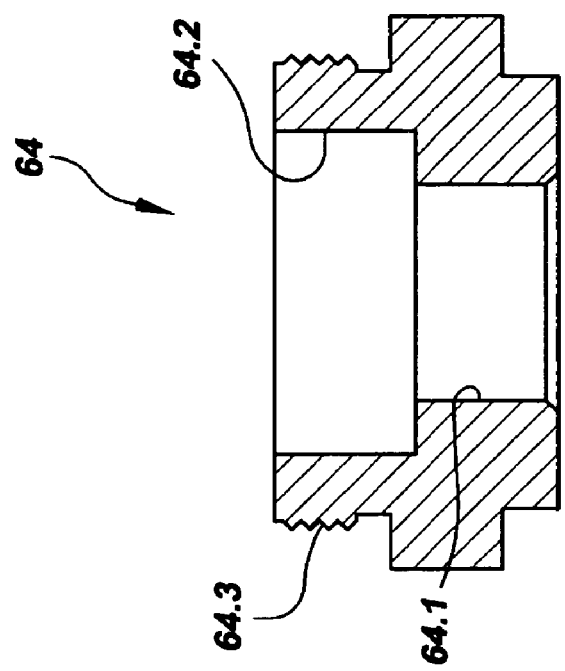
FIG. 13
FIG. 14

METHOD FOR PRODUCING DENTAL RESTORATION AND APPARATUS THEREFOR

CROSS-REFERENCE TO RELATED APPLICATIONS

This application claims the benefit under 35 U.S.C. §119 (e) of U.S. provisional patent application Ser. No. 60/478,209 filed Jun. 13, 2003.

TECHNICAL FIELD

The present invention relates generally to a method for producing a dental restoration, and more particularly to a method wherein a tooth preparation area is scanned either directly or indirectly, the scanned data being used to create one or more molds for preparing a suitable dental restoration, and wherein a suitable dental restorative material is pressed or injected into the mold or molds to form the desired dental restoration. Novel apparatus is further disclosed which may be used in the practice of the method.

BACKGROUND OF THE INVENTION

Processes for forming dental restorations currently used involve various techniques. One of two common techniques is a lost wax process, and the other is computer modeling and milling.

Initially, as used in this document the terms set forth below have the following meanings:

The term "tooth" may refer to one or more teeth. Similarly, the term "tooth preparation area" may refer to a single tooth which has been prepared for the receipt of a dental restoration, or to several teeth, as well as to the surrounding area.

The term "dental restoration" will apply to inlays, onlays, veneers, crowns, and bridges. In addition, it may also apply to copings.

The term "stone model" as used in this specification refers to a model of the tooth preparation area cast from an impression. The "stone model" may be made from a specially calcined gypsum derivative similar to plaster of paris, but which is stronger than plaster of paris.

The term "computer" may apply to one or more computers.

The lost wax technique, while providing a very good dental restoration, is both time consuming and requires skilled craftsmen to produce an acceptable product. One of these lost wax processes utilizes IPS Empress® kits which produce a very high quality dental restoration.

The computer modeling and milling technique essentially utilizes scanned digitized images of the area which is to be restored, and then creates a dental restoration by milling suitable materials. One computer may be associated with the scanning apparatus, another computer with the milling machine, and yet another computer may process the scanned data to produce the 3D image of the dental restoration. All of these functions could conceivably be done in the same computer, which computer can be wired to the scanning station and the milling station.

U.S. Pat. No. 5,452,219, discloses a method of mold manufacture via a computer controlled milling machine, which mold is used for the preparation of dental restorations. The patent discloses the steps of scanning a tooth model in order to obtain data of the three-dimensional surface of the model, processing the data to create a tool path program, and using the program to control the direct fabrication of a tooth mold which is the negative image of the tooth model. The mold then may be used to make an artificial tooth. However, the mold is not suitable for use when molding with high temperature ceramics.

SUMMARY OF THE INVENTION

This invention simplifies the production of high quality dental restoration of the type produced by the IPS Empress® kits. It is a feature of this invention that investment blocks are provided suitable for use in an oven heated to a range of 800°–1,200°, and an ingot of a suitable dental restoration material is also provided. A prepared tooth is scanned, either directly or indirectly, to obtain a digitized three dimensional image of the tooth preparation surface. A 3D computer model of a desired dental restoration is then created, the computer utilizing the scan of the tooth preparation area and data stored in computer memory. Using a computer controlled milling apparatus, the investment blocks are milled to produce a mold shape in the form of the 3D computer model of the desired dental restoration. The investment blocks are then pressed together to produce an investment mold. The investment blocks and the ingot of dental restoration material are then heated to a temperature sufficiently high to permit dental restorative material to flow. The dental restorative material is then pressed from the ingot into the investment mold to form the dental restoration. Next, the mold and pressed dental restoration are cooled. After cooling, the dental restoration is removed from the mold.

BRIEF DESCRIPTION OF THE FIGURES

FIG. 13 is a bottom view of the upper clamping structure.

FIG. 14 is a sectional view taken along line 14—14 in FIG. 13.

DETAILED DESCRIPTION

The dental restoration produced by this method may be a full size dental restoration, or it may be undersized. In addition, the dental restoration may be formed of a single restorative material. Alternatively, it may be a two part dental restoration where an initial restorative material is first molded, and then a second overlying restorative material is molded onto the first underlying restorative material. This form of restoration will be referred to as a compound restoration. A bridge, in addition to other dental restorations, may be compound restoration. Thus, in a bridge it may be desirable to have an initial underlying portion formed of a very strong restorative material, and a second overlying restorative material of glass-ceramic which more closely conforms to the desired appearance.

If the dental restoration is of full size, then it is necessary only to stain and glaze the dental restoration to give it the desired appearance. If undersized, it will be necessary for a lab technician to apply one or more layers of a suitable material to build up the dental restoration to the desired final size and to also give it the desired appearance and translucency. Typically, if the dental restoration is for anterior teeth, it will be layered. Other dental restorations, where the appearance is not as critical, may be merely stained.

Figure 1:
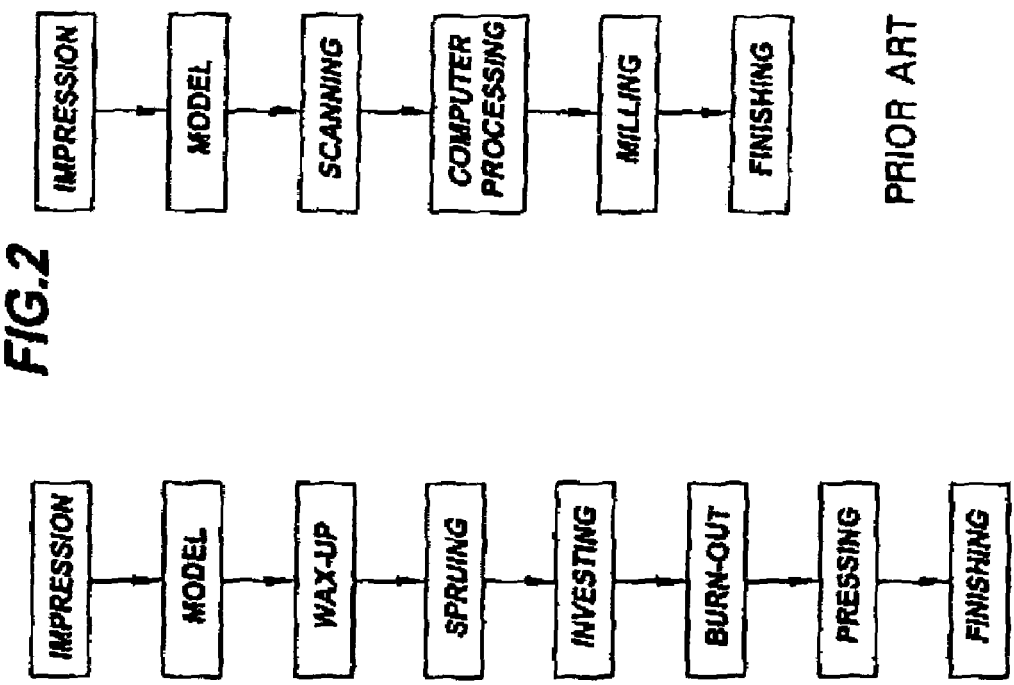
FIG. 1 is a flow diagram showing how an impression may be made using the prior art IPS Empress® process.

With reference first to FIG. 1, a flowchart of the process employed with the IPS Empress® kit is illustrated. In accordance with this prior art process, after the dentist has prepared the tooth for the dental restoration, an impression of the tooth preparation area is made. From the impression, a hard stone model is made. Using the hard stone model, a dental technician will create a wax model of the dental restoration. Now the technician will attach a wax sprue (ingate) to the wax tooth model. A sprue base is provided which has a generally circular base portion and an upwardly extending cylindrical portion which will act to form a guide for a press plunger or piston. The sprue and wax model are now attached to the top of the cylindrical portion of the sprue base. A paper cylinder is now placed on the sprue base about the wax model and sprue. A stabilizing ring is then placed on the top of the paper cylinder. Investment material is then poured into the paper cylinder about the upwardly extending cylindrical portion, the wax dental model, and sprue. The stabilizing ring is then removed and a ring gauge is placed on the paper cylinder. The investment material will set at room temperature, typically 30 minutes to an hour, the set investment material being called an investment ring. The ring gauge and sprue base are removed from the investment ring, shown at 12 in FIG. 4. The investment ring is now placed in an oven along with a press plunger or piston, the oven having been preheated to about 850° C. The investment ring is left in the oven for a length of time sufficient for all wax to vaporize, leaving no residue.

Figure 4:
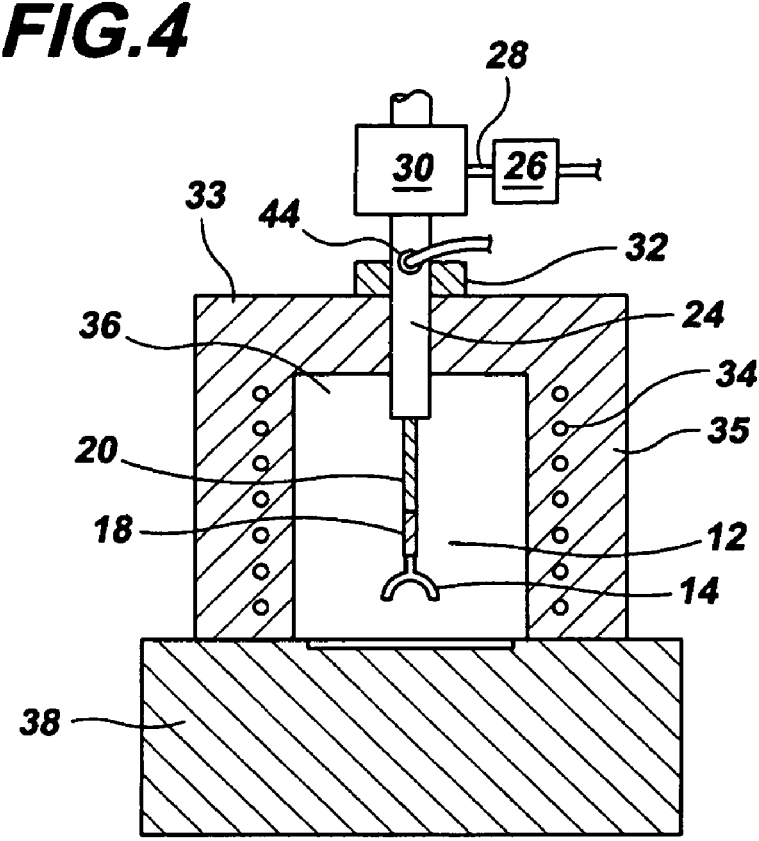
FIG. 4 shows a prior art press that may be used for creating a dental restoration.

After this step has been completed, the hot investment ring 12, ingot 18, and press plunger 20 are placed in a press oven of the type shown in FIG. 4, the furnace being on a base 38. The furnace includes a top 33 and side walls 35. (The oven door is not shown.) The inner chamber 36 of the furnace is heated by a spiral heater 34. A piston assembly 24 is carried by the top wall 33. In the illustrated embodiment the piston assembly is powered electrically though motor 26, rotary output shaft 28, and suitable mechanism 30. However, other forms of power may be employed for the piston assembly 24. The oven is closed and is heated to a higher temperature, typically in the range of 800°–1,200° C. The piston assembly 24 extends through a seal 32 so that a vacuum can be maintained in the inner chamber 36. During heating of the ingot 18, and after it has softened, it is pressed into the mold to form the desired dental restoration. After the restoration mold has been filled with the dental restorative material from the ingot, the investment ring is removed from the furnace and is allowed to cool to room temperature. The dental restoration is divested from the investment ring, typically by "sand" blasting, the "sand" blasting equipment typically using small glass beads. The dental restoration is now finished. The finishing may include either staining or layering, and these techniques are well known to those skilled in the art.

It can be seen that the above process is time consuming and requires a skilled technician to produce the desired results. However, the product of this process is widely accepted, both because of its appearance and also because the margins of the dental restoration tend to closely conform with the prepared tooth.

Figure 3:
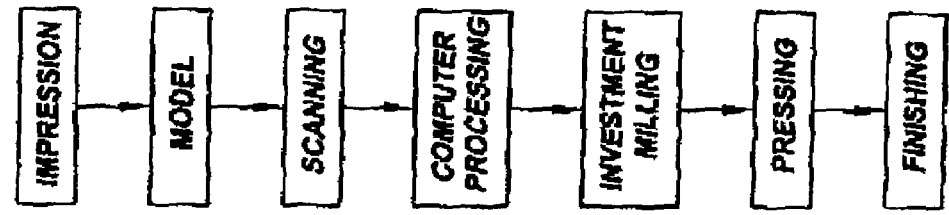
FIG. 3 is a flow chart showing many of the steps disclosed in this application.
Figure 2:
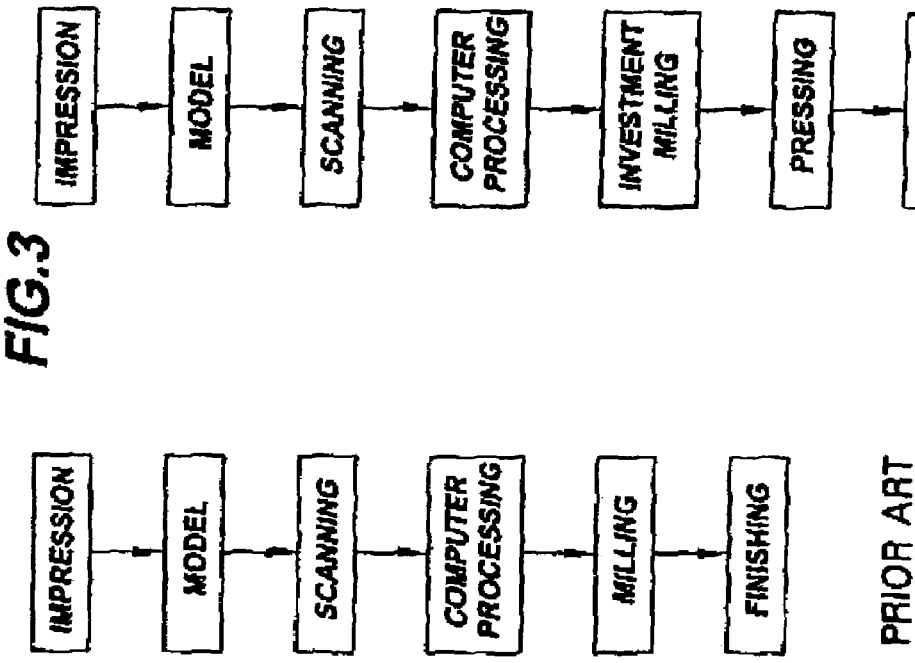
FIG. 2 is a flow chart showing how a dental restoration may be made using prior art CAD-CAM processes.

It has been proposed to create dental restoration by a differing process. In this process, which is seen from the flow chart of FIG. 2, an impression is taken of the tooth preparation area, and a stone model is then formed from the impression. After the model has hardened, it is scanned to create a 3D computer image. It is also known that the scanned image can be taken directly in the patient's mouth, or directly from the impression. In any event, the scanned image is then matched with a tooth form from a library of tooth forms within the computer to create the desired dental restoration. After this step has been completed, the 3D computer image of the dental restoration is sent to a mill where the final dental restoration is milled. In practice, the material from which the dental restoration is milled is very hard material, such as ceramic material formed of zirconium oxide or the like. There are advantages to this system in that the highly skilled technician is not required for sculpting the wax model. In addition, there are time savings. However, when practicing this process it has been found that the appearance of the dental restorations are not of the same quality as the dental restorations produced with the Empress® kits, and there are not always good margins.

Figure 5:
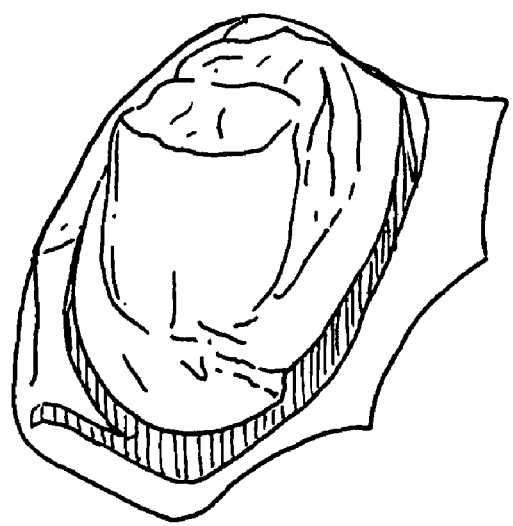
FIG. 5 shows a computer generated scanned image of a first tooth preparation area.
Figure 6:
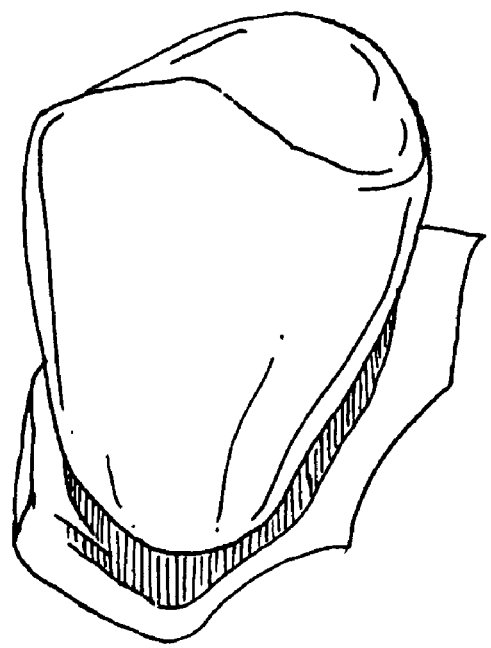
FIG. 6 shows a further computer processed image.
Figure 7:
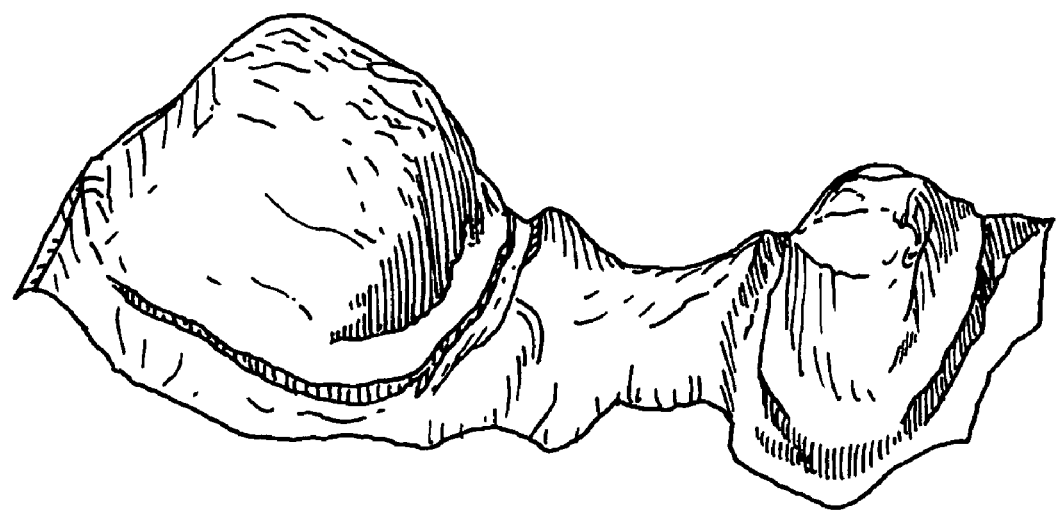
FIG. 7 shows a computer generated 3D image of a second tooth preparation area, which area includes several teeth.
Figure 8:
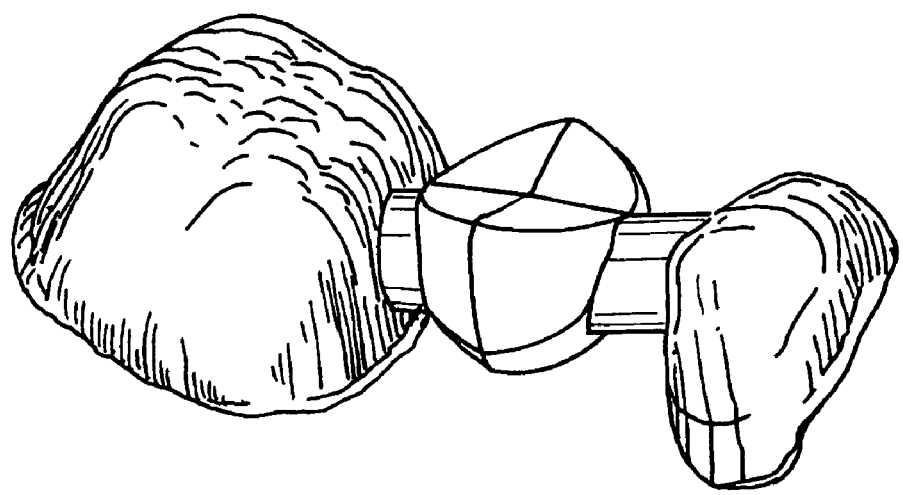
FIG. 8 shows a reduced size 3D dental restoration in the form of a coping for the second tooth preparation area, which coping is molded separately.
Figure 9:
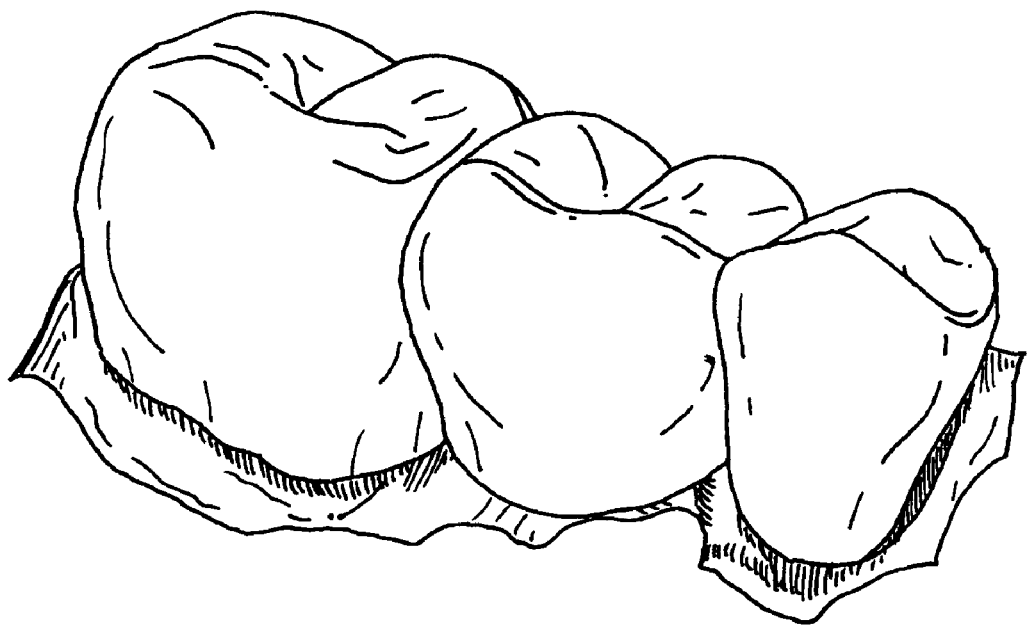
FIG. 9 shows a further 3D computer processed image of a further dental restoration which will overlie the coping dental restoration produced from the 3D image shown in FIG. 8.

In accordance with the principles of this invention, a scan will be made of the tooth preparation area in a manner similar to the prior art, either directly or indirectly. A 3D digitized image of the scanned data is then produced by the computer associated with the scanning equipment, such as the 3D images shown in FIGS. 5 and 7. A graphic 3D model of the dental restoration will then be created from the scanned data and from a library of tooth forms within the computer. This may require some selection of tooth forms by the operator of the computer, and the 3D image of the dental restoration so created will be available for inspection on a suitable terminal, such a 3D image of the dental restoration being shown in FIG. 6, namely a 3D model of a dental restoration which has been created for use with the scanned image of the dental restoration area of FIG. 5. It should be noted that this 3D image has two surfaces, one (not shown) corresponding to the scan of the tooth preparation area, and the other corresponding to the desired anatomical appearance of the tooth as can be seen in the mouth. The 3D image may be of a full size dental restoration, if it is desired to only stain the dental restoration, but it may be undersized if it is to be layered with additional materials by the dental technician. The library of data within the computer will have both full size and undersized dental restorations stored within it. If the restoration is to be of a bridge, it will be necessary for the operator to select more than one tooth restoration from the computer memory in order to build the bridge. In addition, if the dental restoration is to be a compound restoration, the computer may first generate a coping 3D image, such as shown in FIG. 8, and then subsequently generate an overlying dental restoration portion as shown in FIG. 9. This portion, like the one shown in FIG. 6, may be either a full size portion of the dental restoration which will merely have to be stained after molding, or it may be a slightly reduced size which will have to have finishing layers applied by a dental technician.

Figure 11:
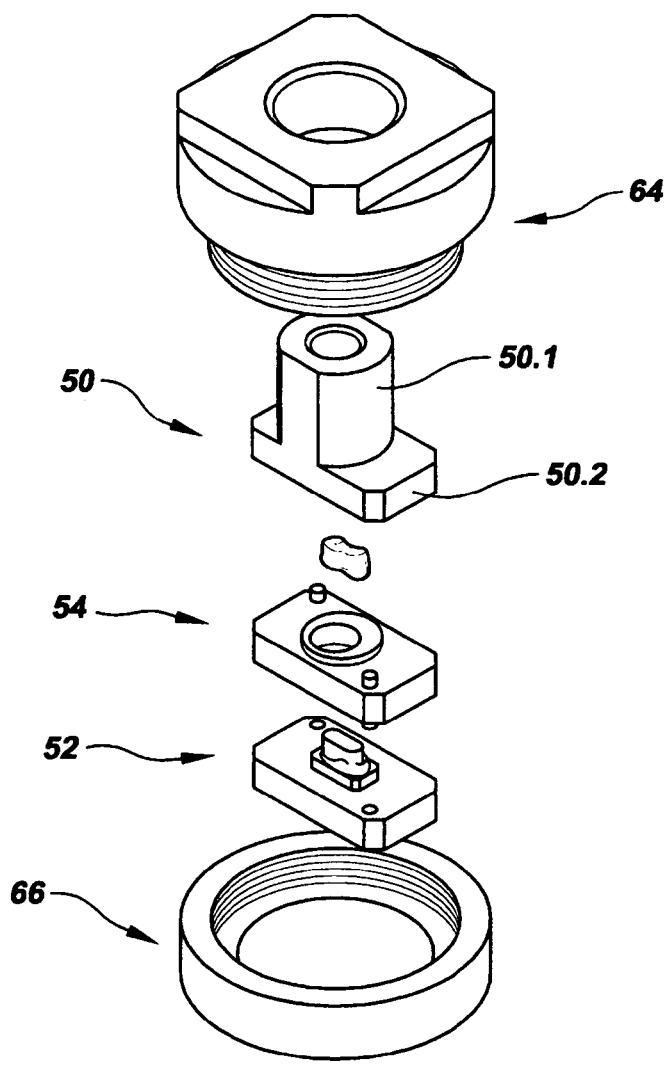
FIG. 11 shows an exploded view of an assembly including upper, intermediate, and lower investment blocks, and upper and lower clamping structures.
Figure 12:
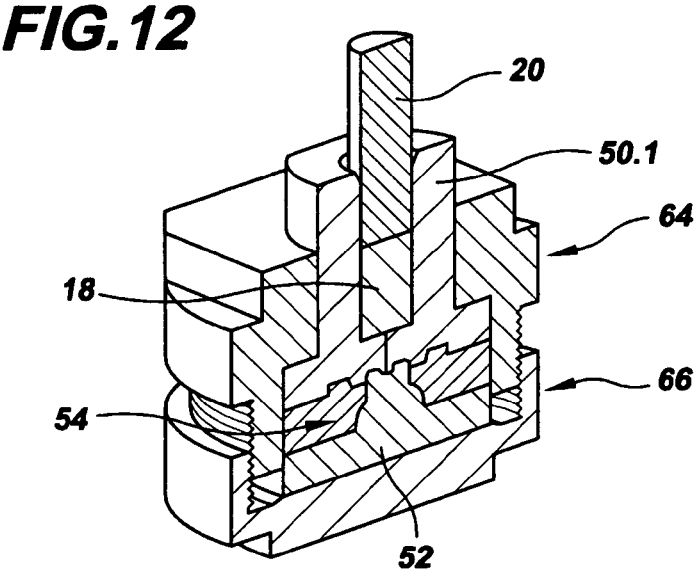
FIG. 12 shows an assembled cross sectional view of the assembly of FIG. 11

It is a feature of this invention that upper, lower, and intermediate investment blocks are provided. In FIGS. 11–12 upper, lower, and intermediate blocks are indicated generally at 50, 52, and 54, respectively. The terms "upper" and "lower" referring to their location in the press oven. While only three blocks are illustrated, additional blocks may be used. The investment block material will be selected to have characteristics similar to the materials used in the Empress® kits which provide good margins, and which may be fired to the temperatures necessary for good flow characteristics of the ingots which will be molded into the molds. Thus, the investment blocks are made from a material of a fine grain size that will permit the milling of margins no greater than 50 microns. The material should be reasonably easy to mill. In addition, the material must be stable at temperatures in excess of that of the press oven. The material should be divestable from the dental restoration without damaging the restoration. In addition, the material should have a coefficient of thermal expansion similar to that of the ingot. One such material is the casting investment material sold by Microstar Corporation of Lawrenceville, Ga., USA under the tradename HS™ Investment. This material is mixed with water in the ratio of 100 gm HS™ Investment to 25 ml water. After initial hand mixing the slurry is placed in a vacuum for a short period of time. It is then further mixed in vacuum for about 1 minute. The slurry is then placed in a mold, the mold and slurry being placed on a vibrator for another 15–20 seconds. After bench setting for about 15 minutes to one hour, the hardened investment block is then removed from the mold and fired at 1600° C. for several hours. After firing, it is suitably cooled.

Figure 10:
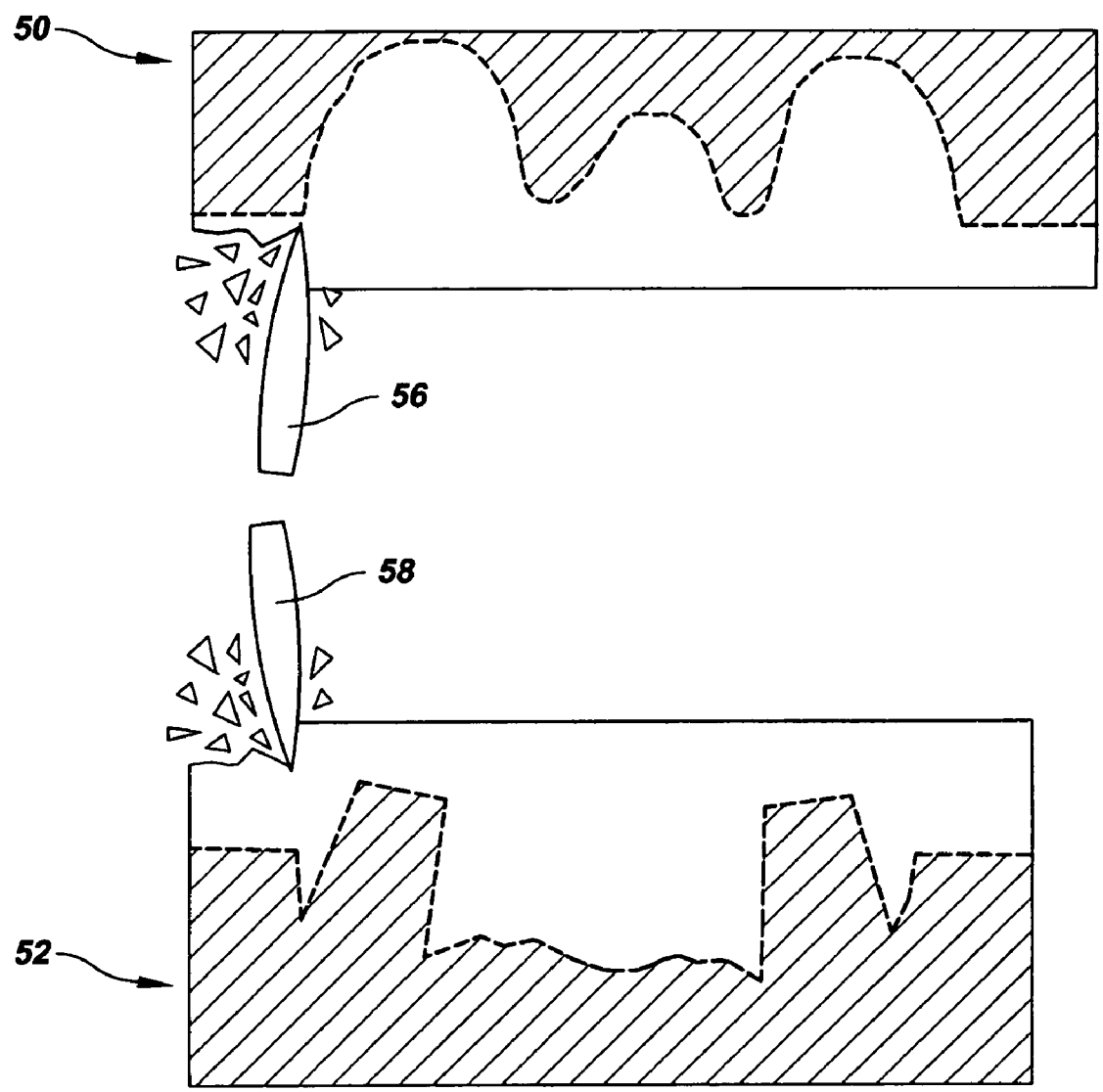
FIG. 10 illustrates the process for milling opposed investment blocks.

As can be seen in FIG. 10, upper and lower investment blocks 50, 52 are milled with tools 56, 58, in accordance with the computer generated 3D graphic model of the dental restoration, the lower investment block typically having milled therein a portion of the surface which will contact the tooth preparation area, and the upper investment block having a portion of the anatomical surface milled therein. The intermediate block 54, or blocks if required from undercuts, will have further portions of the surfaces milled thereon. The suitable milling tool 56, 58 may be a burr or the like. As can be seen from FIGS. 11–12, the upper portion 50.1 of the investment block 50 is provided with a cylindrical cavity 60 for receiving the ingot 18 and the press plunger or piston 20. The upper and lower portions 50.1, 50.2 also having one or more suitable sprues (not shown) milled therein.

After the upper, lower, and intermediate investment blocks have been milled to provide the suitable mold cavity 14 for the dental restoration, the parts are pressed together as can be seen from FIG. 12. Thus, upper and lower clamp rings, indicated generally at 64 and 66, respectively, are provided. The clamp rings are provided with suitable cavities 64.1, 64.2, and 66.1 for snugly receiving associated portions of the investment blocks 50, 52, 54. In addition, the clamp rings are provided with suitable threads 64.3 and 66.2. The clamp rings are made of a material having high thermal conductivity, and good mechanical stability at the temperatures, employed, for example up to 1,200° C. In addition, the clamp rings should be of a material which may be cycled numerous times. Suitable materials include stainless steels, copper nickel alloys and copper tungsten alloys.

The investment blocks 50, 52, 54 are stacked on the lower clamp ring 66, and then the upper ring 64 is secured thereto to tightly clamp the blocks together. As shown, the rings are provided with threads 64.3 and 66.2 for this purpose. However, any other suitable form of device can be used to bring the clamping rings together to hold the blocks together. For example, the furnace may carry a further press mechanism, similar to the piston rod 24, but which is capable of independently bearing upon the upper surface 50.3 of the upper investment block 50.

An ingot 18 of a suitable dental restoration material is then placed in the cylindrical cavity of the upper portion 50.1 of the upper investment block 50. The ingot may be of any suitable dental restorative material such a glass, glass-ceramic, or a metal material which softens in the range of 800–1,200° C. A press plunger or piston 20 is placed above the ingot. The parts are now placed in a press oven similar to the type shown in FIG. 4. The ingot is then brought up to the desired temperature and is pressed into the mold cavity 14 to produce the restoration. A pressure sensor 44 may be employed to insure that the correct pressure is used. After this step is completed, the parts are then processed further in a manner similar to the manner used with the prior art Empress® kits. Thus, after parts have been removed from the oven and suitably cooled, the investment blocks are removed from the dental restoration, indicated generally at 70 in FIG. 11, by "sand" blasting. While "sand" blasting may be employed to divest the mold from the dental restoration, it is possible that other techniques may be used. For example, the investment mold may be struck a sharp blow, causing to shatter away from the restoration. Other techniques known to those skilled in the art may also be used.

If a compound restoration is being formed, it will be necessary to mill a first upper, lower and intermediate investment blocks, and then to use the process outlined above to form an underlying or coping portion of the dental restoration, such as that shown in FIG. 8. Next, second upper, lower and intermediate investment blocks will be milled, which blocks will receive the underlying or coping portion. A second ingot will then be used, this ingot having a lower melting temperature than the coping, the restorative material of the second ingot then being pressed again in a manner similar to that previously discussed, but this time it will bond to the coping to form a compound restoration. While conceivably the process could be reversed, with the coping being molded during the second molding operation, this would require that the sprues contact that surface which will mate with the tooth preparation area. This is undesirable as there would be residue from the sprues on this surface, which residue would be very difficult to remove properly. Therefore, it is preferred that the sprues extend to the anatomical surface.

It is a further feature of this invention that the computer may be used to mill a model of the tooth preparation area for the convenience of the dental technician. Thus, during the final processing by the dental technician, it is customary to mount the dental restoration on a model.

The benefits of the above process are that it: saves time and labor; utilizes existing equipment; remake time is greatly reduced; minimizes technician errors; and the finished product is a high quality dental restoration, such as for example an IPS Empress® dental restoration, but not limited thereto. Furthermore, it eliminates the steps of wax-up, spruing, investing, and burnout.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. The terms "upper" and "lower" are used for convenience only and should not be interpreted as limiting.

What is claimed is:

1. A method of making a dental restoration comprising the following steps:
   scanning a tooth preparation area, either directly or indirectly, to obtain a digitized three dimensional image of the surface of the tooth preparation area;
   creating a 3D computer model of a desired dental restoration which has a tooth preparation area surface utilizing the scan of the tooth preparation area and data stored in computer memory;
   characterized by
   providing two or more investment blocks suitable for use in an oven heated to a range of 800°–1,200° C.;
   providing an ingot of a suitable dental restorative material selected from the group consisting of glass, glass-ceramic, or a metal which softens in the range of 800–1,200° C.;
   using a computer controlled milling apparatus, milling the investment blocks to produce a mold shape in the form of the 3D computer model of the desired dental restoration;
   pressing the investment blocks together to produce an investment mold;
   heating the investment blocks and the ingot of dental restoration material to a temperature sufficiently high to permit dental restorative material to flow;
   causing the dental restorative material to flow into the investment mold to form the dental restoration;
   cooling the mold and pressed dental restoration; and
   removing the dental restoration from the mold.

2. The method according to claim 1 further including the steps of providing an upper investment block with an upper cavity for receiving the ingot; and placing the ingot into the upper cavity of the upper investment block prior to the step wherein the dental restorative material is pressed into the mold.

3. The method according to claim 1 wherein the computer controlled milling apparatus is also used to mill proper sprues in the upper investment block.

4. The method according to claim 1 wherein the step of scanning the prepared tooth to obtain a digitized three dimensional image of the prepared surface is done within the mouth.

5. The method according to claim 1 wherein an impression is made of the prepared tooth and the step of scanning the prepared tooth to obtain a digitized three dimensional image of the prepared surface is done on the impression.

6. The method according to claim 1 wherein an impression is made of the prepared tooth, and further including the step of making a hard stone model from the impression, and wherein and the step of scanning the prepared tooth to obtain a digitized three dimensional image of the prepared surface is done from the hard stone model.

7. The method according to claim 1 wherein the dental restoration is removed from the mold by abrading the investment mold away from the dental restoration.

8. The method according to claim 1 wherein the dental restoration is a coping for a compound dental restoration, the method further including the steps of making an overlay portion for the compound dental restoration; the method further being characterized by the additional steps of
   providing further upper and lower investment blocks suitable for use in an oven heated to a range of 800°–1200° C.;
   providing a further ingot of a suitable dental restorative material, the further ingot having a lower melting temperature than the coping made in claim 1;
   using a computer controlled milling apparatus, milling the further investment blocks to produce a mold shape in the form of the 3D model of the desired compound dental restoration;
   placing the coping in the milled investment blocks, leaving a space for the overlying dental restoration portion;
   pressing the investment blocks together to produce an investment mold;
   heating the further investment blocks and the further ingot to a temperature sufficiently high to pennit dental restorative material of the further ingot to flow;
   causing the dental restorative material from the further ingot to flow into the mold to form the compound dental restoration, the material from the further ingot bonding to the coping to form the compound restoration;
   cooling the mold and pressed compound dental restoration; and
   removing the compound dental restoration from the mold.

9. An apparatus useful for pressing investment molds together in an oven heated to 800–1,200° C., the apparatus including
   a lower clamp ring having a threaded collar portion and a cylindrical cavity within the collar portion; and
   an upper clamp ring having a lower threaded portion and a cavity, the cavity being so sized that it will snugly receive investment blocks which are to be clamped together in such a manner that the investment blocks cannot turn with respect to the upper clamp ring.

10. A method of making a dental restoration comprising the following steps:
   scanning a tooth preparation area, either directly or indirectly, to obtain a digitized three dimensional image of the surface of the tooth preparation area;
   creating a 3D computer model of a desired dental restoration which has a tooth preparation area surface utilizing the scan of the tooth preparation area and data stored in computer memory;
   characterized by
   providing at least an upper, intermediate, and lower investment block suitable for use in an oven heated to a range of 800°–1,200° C.;
   providing an ingot of a suitable dental restorative material selected from the group consisting of glass, glass-ceramic, or a metal which softens in the range of 800–1,200° C.;
   using a computer controlled milling apparatus, milling the investment blocks to produce a mold shape in the form of the 3D computer model of the desired dental restoration;
   pressing the investment blocks together to produce an investment mold;
   heating the investment blocks and the ingot of dental restoration material to a temperature sufficiently high to permit dental restorative material to flow;
   causing the dental restorative material to flow into the investment mold to form the dental restoration;

cooling the mold and pressed dental restoration; and removing the dental restoration from the mold.

11. The method according to claim 10 further including the steps of providing the upper investment block with an upper cavity for receiving the ingot; and placing the ingot into the upper cavity of the upper investment block prior to the step wherein the dental restorative material is pressed into the mold.

* * * * *